US005658732A

United States Patent [19]

Ebersole et al.

[11] Patent Number: 5,658,732
[45] Date of Patent: Aug. 19, 1997

[54] ASSAY METHOD FOR BIOLOGICAL TARGET COMPLEXES ON THE SURFACE OF A BIOSENSOR

[75] Inventors: Richard Calvin Ebersole, Wilmington, Del.; John Richard Moran, Kennett Square, Pa.; Michael David Ward, Newark, Del.

[73] Assignee: E. I. Du Pont de Nemours and Company, Wilmington, Del.

[21] Appl. No.: 397,026

[22] Filed: Mar. 1, 1995

Related U.S. Application Data

[63] Continuation of Ser. No. 52,834, Apr. 27, 1993, abandoned, which is a continuation of Ser. No. 417,102, Oct. 4, 1989, abandoned.

[51] Int. Cl.$^6$ .......................... C12Q 1/68; G01N 33/551; G01N 30/96; C12N 15/00
[52] U.S. Cl. .................................. 435/6; 435/4; 435/7.1; 435/7.8; 435/721; 435/7.92; 435/7.94; 436/524; 436/525; 436/531; 436/532; 436/537; 436/547; 436/149; 436/151; 436/806; 935/77; 935/78; 422/68.1; 422/69
[58] Field of Search ........................... 435/4, 6, 7.1, 7.8, 435/7.21, 7.92, 7.94; 436/524, 525, 531, 532, 537, 547, 149, 151, 806; 422/68.1, 69

[56] References Cited

U.S. PATENT DOCUMENTS

| | | | |
|---|---|---|---|
| 4,236,893 | 12/1980 | Rice | 23/230 B |
| 4,299,916 | 11/1981 | Litman et al. | 435/6 |
| 4,314,821 | 2/1982 | Rice | 23/230 B |
| 4,735,906 | 4/1988 | Bastiaans | 436/527 |
| 4,999,284 | 3/1991 | Ward et al. | 435/4 |
| 5,135,852 | 8/1992 | Ebersole et al. | 435/39 |
| 5,362,653 | 11/1994 | Carr et al. | 436/165 |
| 5,501,986 | 3/1996 | Ward et al. | 436/525 |

FOREIGN PATENT DOCUMENTS

| | | |
|---|---|---|
| 239613 | 9/1985 | European Pat. Off. . |
| 0201079 | 11/1986 | European Pat. Off. . |
| 215669 | 3/1987 | European Pat. Off. . |
| 276142 | 7/1988 | European Pat. Off. . |
| 295965 | 12/1988 | European Pat. Off. . |
| 0311768 | 4/1989 | European Pat. Off. . |
| 8909937 | 10/1989 | WIPO . |
| 9004786 | 5/1990 | WIPO . |

OTHER PUBLICATIONS

Syvanen et al., Nuc. Ac. Res., vol. 14, No. 12, 1986, pp. 5037–5048.
"New Route to biosensors", C & E News, Apr. 30, 1990, p. 28.
Ebersote et al., "Spontaneously formed functionally Active Avidin Monolayers on Metal Surfaces", 112 JACE 3239–3241 (1990).
J. Sklar, "DNA Hybridization in Diagnostic Pathology", Human Path., 16, 654 (1986).
M.J. Gore, Clin. Chem. News, 12, 1 (1986).
Dunn et al., Gene, 21, 77–85 (1983).
M. Ranki et al., Gene, 21, 77–85 (1983).
M. Ranki et al., Curr. Top. Microbiol. Immunol., 104, 307–318 (1983).
Virtanen et al., The Lancet, 1, 381–383 (1983).
A.M. Palva, Jrl. of Micro., 18, 92–100 (1983).
J. Meinkoth et al., Anal. Biochem. 138, 267–284 (1984).
Hames et al., eds., "Nucleic Acid Hybridizations," IRL Press, 1985.
Giulbault et al., Biotechnology, 7, 349–351 (1980).
Maniatis et al., eds., "Molecular Cloning: Laboratory Manual", Cold Spring Harbor publisher 1986.
Ruth et al., DNA 4, 93 (1985).
McGeoch et al., Jrl. Gen. Virol., 69, 1531–1574 (1988).
McGeoch et al., Jrl. Mol. Biology, 181, 1–13 (1985).
Chu et al., Nucleic Acids, Res. 16, 3671–3691 (1988).
Langer et al., Proc. Natl Acad. Sci. USA, 78, 6633–6637 (1981).
Alves et al., Nucleic Acids Res., 16, 8722 (1988).
Ghosh et al., Analytical Biochem., 178, 43–51 (1989).
E. Jablouski et al., Nucleic Acids Research, 14, 6115–6128 (1986).
P. Li et al., Nucleic Acids Res., 15, 5275–5287 (1987).
Miller et al., J. Clin. Microbiology, 26, 1271–1276 (1988).
Tijssen, "The Theory and Practice of Enzyme Immunoassay", Elsevier, N.Y., N.Y., p. 331 (1985).
Raether, H., "Surface Plasmons"; Springer–Verlag, New York (1988).
Hahn et al., Nature 302, 166 (1984).
Ruth et al., Fed. Proceedings, 44, 1622 (1985).
Ngeh–Ngwainbi et al., J. Amer. Chem. Soc., 108, 5444–5447 (1986).
Flowers et al., Fed. Proc. 45(6), 1516 (1986).
Fawcett et al., Anal. Lett., 21(7), 1099–1114 (1988).
Shons et al., J. Biomed. Mater. Res., 6, 565–570 (1972).
Guilbault et al., "Analytical Uses of Piezoelectric Crystals: A Review", in CRC Critical Review in Analytic Chemistry, 19(1), pp. 1,3,28 (1988).
Grabbe et al., J. Electroanal. Chem., 1987, 223, 67–78.
Roederer et al., Anal. Chem., 1983, 55, 2333–2336.
Ebersole et al., J. Amer. Chem. Soc. 110, 8623 (1988).
T. Maniatis et al., "Molecular Cloning", Cold Spring Harbor Laboratory, 1982.
Wilchek et al., Analytical Biochemistry, 171:1–32 (1988).

*Primary Examiner*—Bradley L. Sisson

[57] ABSTRACT

A biosensor detector method for detecting biological targets, using specific binding, or hybridization techniques coupled with enzymatic amplification and the mass sensing capability of a piezoelectric oscillator. An optical biosensor is also contemplated.

9 Claims, 3 Drawing Sheets

ASSAY METHOD FOR BIOLOGICAL TARGET COMPLEXES ON THE SURFACE OF A BIOSENSOR

This application is a file-wrapper continuation of Ser. No. 08/052,834, filed on Apr. 27, 1993, abandoned, which is a file wrapper continuation of Ser. No. 07/417,102, filed on Oct. 4, 1989, abandoned.

FIELD OF THE INVENTION

This invention relates to a biosensor assay method for detecting biological targets. More specifically, the method uses specific binding or hybridization techniques coupled with enzymatic amplification and the mass sensing capability of a piezoelectric oscillator.

BACKGROUND OF THE INVENTION

Immunoassay methodology for the diagnostic determination of biological analytes (drugs, enzymes, metabolites, hormones, antigens, etc.) has proven valuable for clinical analyses, primarily because of the highly specific recognition between analytes and antibodies elicited for those analytes. Although extensively used, the cost and time intensiveness of these methods and the safety hazards of radioimmunoassay have prompted investigations of new techniques. Much attention has been given to "biosensors" in which an immunological reaction that occurs at the interface of a transducer results in output of an electrical signal. Critical features of biosensors are low cost, simplicity, disposability, and sensitivity.

Nucleic acid hybridization tests, which make use of specific polynucleotide probes, provide a means of detecting specific sequences of nucleic acids in test samples and thereby provide important new clinical diagnostic capability. For example, susceptibility to a disease as well as the identity of organisms which might be involved can be evaluated. Hybridization tests have established relationships between viral infections and cancer. Prenatal diagnosis of genetic disease and detection of inherited disease traits have been reported. Applications for the identification of slow growing and resistant infectious organisms have been reported. (Skylar, "DNA Hybridization in Diagnostic Pathology", Human Path., 16, 654 (1986)).

Mixed-phase hybridization systems typically have been used to perform these types of tests. In testing, the hybridizations are performed on membranes (solid phase), usually consisting of nylon or nitrocellulose. As such, the tests are quite cumbersome involving complicated multistep procedures. For example, the assays usually involve loading a membrane with a nucleic acid sample by fixing the nucleic acid to the membrane (if DNA, it must be denatured to create single-stranded molecules) and then saturating the remaining membrane attachment sites with heterologous nucleic acids to prevent the probe reagent from sticking to the membrane in a nonspecific manner. All of these steps must be done before performing the actual hybridization with reporter reagents. The conventional membrane based test procedures are time consuming, taking 4–24 hours to perform, burdensome and complex, requiring multiple reagent additions, wash procedures, and labor intensive manipulations. (Gore, Clin. Chem. News, 12, 1 (1986)).

Furthermore, membrane-based hybridizations cannot always be used directly for crude samples. The membranes are subject to clogging. Moreover, crude samples contain proteins, lipids, mucopolysaccharides, etc., which compete for binding sites on the membranes, reduce the binding capacity of the membrane and contribute to nonspecific binding of reporter reagents. These competing interactions cause unacceptable background and diminished test response. Furthermore, the nucleic acid is typically found only in minute quantities ($<10^{-15}$M) in most test samples, since only a few copies of target DNA are present in each cell. Therefore, for clinical diagnostic applications the nucleic acids must be partially purified and concentrated prior to testing.

A number of new hybridization techniques circumventing these drawbacks have been reported in the literature. The sandwich hybridization technology on various supports has reduced sample pretreatment complexity and decreased the number of procedural steps.

Despite simplified sample pretreatment, sandwich assays continue to suffer from long equilibration times, procedural complexity and limited sensitivity. This results from the concentration dependence of the hybridization reactions which dictate that longer equilibration times are required at lower target concentrations (discussed in "Nucleic Acid, Hybridizations.", B. D. Hermes and D. J. Higgins, eds., IRL Press, 1985), and the insensitivity associated with various instruments and procedures for detection of reporter probe reagents.

Sandwich hybridizations require two independent hybridization events. The reactions times are influenced by both the reporter probe and capture reagent concentrations. Furthermore, the reaction rates are known to be slower on solid phase reagents than would occur in solution. It is therefore desirable to have a test method in order to shorten the assay time. A desirable advance would be a test method that permits each hybridization to take place in solution.

Hybridization assays and immunoassays are severely limited for both diagnostic and research applications by the lack of detection sensitivity. Generally, only a few copies of target gene sequences or target analyte are found in samples of clinical interest. For example, clinically important, infectious disease specimens generally contain between 1 and $10^6$ infectious organisms. Since each organism contains only a few copies (4 to 100) of a specific sequence of genetic information per cell, the total target DNA available ranges from $10^{-15}$ to $10^{-20}$ moles. This is below the detection limit of many hybridization methods. For this reason, probe tests generally have not been used for direct specimen testing, but have been useful for testing specimens in which the number of microbes has been increased by culturing or replicating the specific gene sequence of interest.

To overcome sensitivity limits, various detection approaches for hybridization assays have been used. One such method relies on radio-labeled reporter reagents, but is widely considered hazardous and impractical. Other detection methods make use of fluorescent tags or enzyme labeling by which fluorescent products are generated. Although these are highly sensitive techniques, detection of fluorescence and luminescence are inherently limited because the intensity of the detection signal is subject to decay from photo bleaching and quenching.

Gene amplification strategies have also been disclosed in the art to increase the sensitivity of probe tests. Gene Probe Inc. described the use of probes directed against RNA target. Since many copies of target RNA can be produced in each cell during the expression of a single copy of DNA, RNA probe tests tend to be inherently more sensitive and thus more useful for direct specimen testing. However, RNA targets are particularly labile and are subject to enzymatic digestion by ribonucleases ubiquitously found in samples.

Cetus Corp. (Emeryville, Calif.) has reported the development of an in vitro gene amplification technique using a polymerase enzyme to multiply the number of DNA copies found in test samples. In this way the number of copies of DNA is greatly increased (ca. a million fold). Once expanded, the target DNA can then be tested using conventional probe analysis techniques. Biotechnolgy News, Oct. 16 (1986). This technique, known as a polymerase chain reaction procedure, involves multiple steps adding time, additional user manipulations, and reagent costs to the overall probe assay.

It is therefore desirable to have a method of detecting hybridization assays which is highly sensitive, less complex than known techniques, can be performed safely, and is not subject to interferences from chemical quenching reactions and light absorbing materials. The instant invention seeks to overcome the above mentioned limitations by exploiting a method of enzyme amplified piezoelectric detection of nucleic acid sequences.

The use of a piezoelectric quartz crystal microbalance (QCM) device has been reported for immunoassay applications and detection of polynucleotide such as DNA. This device consists of a single quartz crystal wafer sandwiched between two metal electrodes. The electrodes provide means of connecting the device to an external oscillator circuit that drives the quartz crystal at its resonant frequency. This frequency is dependent on the mass of the crystal, as well as the mass of any layers confined to the electrode areas of the crystal. Changes in mass on the surface of the electrode thus change the frequency of the QCM. The changes in the resonant frequency of these devices can be correlated to the amount of mass change. If the quartz crystal and any attached layers are presumed to obey rigid-layer behavior, the mass change can be determined from the frequency change by the Sauerbrey relationship.

Sauerbrey Equation $$\Delta f = \frac{2f_0^2 \Delta m}{A \sqrt{\rho_q \mu_q}}$$

where $\Delta f$ is the measured frequency shift, $f_0$ the parent frequency of the quartz crystal, $\Delta m$ the mass change, $A$ the piezoelectrically active area, $\rho_q$ the density of quartz (2.648 g cm$^{-3}$) and $\mu_q$ the shear modulus (2.947×10$^{11}$ dynes cm$^{-2}$ for AT-cut quartz).

Applications of the QCMs to immunoassay and hybridization generally involve attaching the first member of a specific binding pair to the surface of the QCM before the actual analysis.

The piezoelectric methods described in the art do not teach means of using enzymes as a means to amplify the piezoelectric detection of polynucleic acids. Detection sensitivity of the art is thus inherently limited by the weight of the specific polynucleic acids or by the increased mass achieved by use of a particle reporter.

Each of these methods involves first determining the resonance frequency of the crystal. A sample suspected of containing the second member of the binding pair is then added under conditions suitable for promoting binding between the two members of the binding pair. The excess sample debris and unbound material is freed from the QCM by washing. Then the crystal is measured prior to or after drying of the crystal.

In EPO 295,965 for example, the mass change is attributed only to the mass increase resulting solely from the binding of the second member of the binding pair to the QCM. Consequently, sensitivity is poor. There is therefore a need in the art for a piezoelectric based hybridization method in which the mass change resulting from the specific binding between the complementary strands can be amplified to provide a more sensitive and reliable assay.

Unlike immunoassays in which the assay conditions can be essentially standardized for different methods and thus more easily automated, hybridization assays require careful consideration of optimum reaction conditions. Complicating the design of a reaction system is the fact that different polynucleotides hybridize under different conditions. For example, denatured DNA in the presence of its complementary strand will hybridize under proper conditions and re-associate into double stranded DNA. The extent of hybridization is related to the degree of complementarity between the two strands, the ionic strength, chain length, polynucleic acid concentrations, temperature and pH of the hybridization media as discussed in "Nucleic Acid, Hybridizations", B. D. Harmes and D. J. Higgins, eds., IRL Press, 1985. As a consequence, optimum hybridization conditions tend to differ for each unique target sequence. The variation in reaction conditions severely complicates the automation of probe tests by requiring means to vary temperature, reaction conditions and timing for each different probe test.

It is therefore desirable to have a piezoelectric nucleic acid hybridization assay that (1) permits hybridization under reaction conditions required for each different hybridization and (2) is performed independent of the conditions for detecting successful hybridizations by the piezoelectric oscillator. This would enable different hybridization assays to be carried out using the same procedure and (or) detected under the same measurement conditions.

A major limitation of the art is that the surface of the piezoelectric crystal must be modified by attaching to it one member of the specific binding pair. As a consequence, each specific test requires a uniquely modified piezoelectric crystal. Receptor reagents are expensive, can be inactivated during the immobilization process and can separate from the solid surface after immobilization. (G. G. Giulbault, J. H. Luong, and E. Pursak-Sochaczewski, Biotechnology, Vol 7, pp 349–351, (1989)). Preparation of the assay reagents can thus be complicated and require unique reaction conditions for each type of analyte. It is therefore of practical advantage to have a sandwich assay system which enables the same immobilized surface capture reagent to be used for all tests regardless of the specific target analyte.

A need also exists for methodology to anchor a surface capture reagent to the electrode surface of the piezoelectric oscillator, thus forming the piezoelectric sensor in the proper format.

It is the purpose of this invention to provide an assay method which is rapid, procedurally uncomplicated and capable of affording both quantitative and qualitative results. The instant invention adopts a sandwich hybridization assay system which enables the same surface capture reagent to be used for all tests regardless of the nucleic acid target. It is also less expensive to use a non-nucleic acid material as a capture reagent on the oscillator.

The instant invention uses a piezoelectric hybridization method which enables the hybridization phases of the assay to be carried out independently of the attachment of surface capture reagents to the piezoelectric oscillator. Therefore, hybridization conditions can be readily varied. Further, the method of this invention permits automation and more effective replication of the tests because the attachment of a target complex to the piezoelectric sensor can be carried out under the same conditions, regardless of the conditions used for hybridization.

SUMMARY OF THE INVENTION

A new and advantageous method for the capture and detection of biological targets is provided by Applicants' invention. The method utilizes a surface capture reagent adsorbed to a biosensor in a sandwich assay to usefully detect nucleic acids, antibodies, and other biological targets. Specifically, one aspect of this invention is an assay method for detecting a target analyte in a sample by means of a piezoelectric sensor comprising the steps of:

(a) immobilizing a surface capture reagent on a surface of a piezoelectric oscillator to form a piezoelectric sensor;

(b) contacting a liquid sample suspected to contain a target analyte with an enzyme reporter conjugate and a bifunctional binder conjugate to form a target complex comprising the enzyme reporter conjugate, the suspected target analyte, and the bifunctional binder conjugate;

(c) capturing the target complex with the surface capture reagent immobilized on the piezoelectric oscillator to form an assay system;

(d) separating uncaptured target complex, enzyme reporter conjugate, and bifunctional binder conjugate from the assay system;

(e) contacting the assay system with a signal generating substrate specific for the enzyme of the target complex to the assay system;

(f) allowing the accumulation on the surface of the piezoelectric oscillator of a signal generating product resulting from the conversion of the signal generating substrate by the enzyme; and (g) monitoring the resonant frequency of the piezoelectric oscillator caused by the accumulation of the signal generating product onto the piezoelectric sensor.

In another aspect, Applicants' invention is an assay method for detecting a target analyte in a sample by means of an optical sensor, comprising:

(a) immobilizing a surface capture reagent on the surface of an optical sensor;

(b) contacting a liquid sample suspected to contain a target analyte with an enzyme reporter conjugate and a bifunctional binder conjugate to form a target complex comprising the enzyme reporter conjugate, the suspected target analyte, and the bifunctional binder conjugate;

(c) capturing the target complex with the surface capture reagent immobilized on the optical sensor to form an assay system;

(d) separating uncaptured target complex, enzyme reporter conjugate, and bifunctional binder conjugate from the assay system;

(e) contacting the assay system with a signal generating substrate specific for the enzyme of the target complex to the assay system;

(f) allowing the accumulation on the surface of the optical sensor a signal generating product resulting from the conversion of the signal generating substrate by the enzyme; and (g) monitoring changes in light propagation caused by the accumulation of the signal generating product onto the optical sensor.

Another aspect of this invention involves the adsorption of a surface capture reagent to a metal surface of the sensor. Another aspect of this invention involves the use of adhesion promoters to attach to surface capture reagent to the sensor.

DETAILED DESCRIPTION OF THE INVENTION

Figure 1:
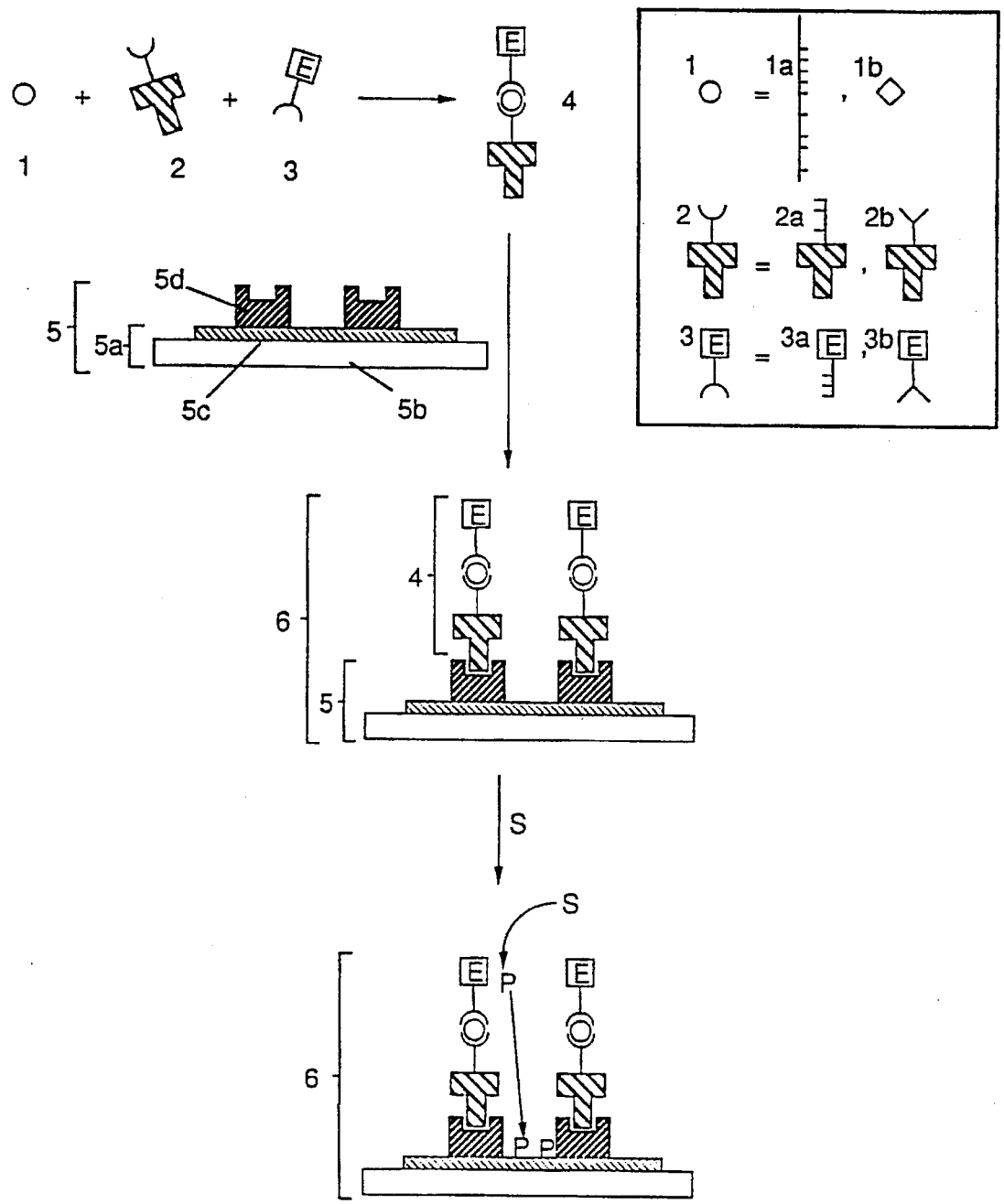
FIG. 1 is a schematic drawing showing the elements and operation of the invention in which the surface capture reagent is immobilized onto a piezoelectric oscillator.

In order to use the method of this invention, one must have 1) conjugate reagents to obtain high recognition specificity for target analytes; 2) suitable reaction conditions for forming a target complex; and 3) methodology for binding the target complex to the QCM surface, and 4) a precise means of detecting the change in mass resulting from build up of signal generating products.

The following terms will be used in the context of this disclosure:

The term "target analyte" refers to the substance to be detected including but not limited to nucleic acids, polynucleotides, drugs, hormones, proteins, enzymes, antibodies, carbohydrates, and antigens. The target analyte must be capable of complementary binding to the reagents. The "enzyme reporter conjugate" is a conjugate of an enzyme and a first capture ligand. The "capture ligand" of the enzyme reporter conjugate may be a polynucleotide recognition sequence which is selected to complex with a sequence within the target analyte whose presence and/or amount is to be determined. The first capture ligand may also be an antibody complementary to a target analyte such as a protein, antigen, blood cell, eukaryate cell, enzyme or other biological unit. The "bifunctional binder conjugate" is a conjugate containing a second capture ligand and a binder capable of specific binding to a surface capture reagent. The second capture ligand may be a polynucleotide sequence which is selected to hybridize specifically with a portion of the target analyte whose presence and/or amount is to be determined. The second capture ligand alternatively may comprise an antibody complementary to the target analyte. "Capture reagent" refers to either the enzyme reporter conjugate, the bifunctional binder conjugate, or both. "Surface capture reagent" refers to the substance immobilized on the surface of the sensor. The surface capture reagent is chosen to specifically bind with the bifunctional binder conjugate. The "sensor" is the instrument, either a piezoelectric sensor or sensor means for measuring optical resolution, to which a surface capture reagent is immobilized. The "piezoelectric sensor" refers to the unit made up of a piezoelectric oscillator upon which the surface capture reagent has been immobilized. The surface capture reagent is capable of binding to the second capture ligand of the bifunctional binder conjugate. The "target complex" refers to the complex formed by the enzyme reporter conjugate, the target analyte, and the bifunctional binder conjugate. "Piezoelectric oscillator" refers to a quartz crystal with attached electrodes. Its vibrational frequency changes as its mass changes. The "signal generating substrate" is a soluble material which is capable of being converted by the enzyme of the enzyme reporter conjugate to a "signal generating product". The signal generating product is capable of interacting with the surface of the piezoelectric sensor, increasing the mass on the surface of the sensor surface and thus producing an amplified shift in the resonance frequency of the piezoelectric sensor. The signal generating product may alternatively induce a secondary reagent to interact with the sensor surface, also producing an amplified shift in the resonance frequency of the piezoelectric sensor. The signal generating product may also interact with a sensor means for measuring optical resolution.

FIG. 1 illustrates the operation of the invention. A target analyte (1) a bifunctional-binder conjugate (2) and an enzyme reporter conjugate (3) are linked by methods appropriate to the particular forms of these elements to form a target complex (4). The target analyte (1) more specifically may be, for example, a nucleotide sequence (1a) or other analyte (1b). The bifunctional-binder conjugate (2) more specifically may comprise, for example, a binder linked to an oligonucleotide sequence (2a) that is complementary to the target analyte (la) or a binder linked to an antibody (2b) that will bind specifically to the target analyte (1b). The recognition elements (2a) and (2b) are known collectively as the second capture ligand. The enzyme reporter conjugate (3) more specifically may comprise, for example, an enzyme (E) and an oligonucleotide sequence unit (3a) that is complementary to the target analyte (1a), or an enzyme (E) and an antibody unit (3b) that will bind specifically to the target analyte (1b). Elements (3a) and (3b) are known collectively as the first capture ligand.

The invention also comprises a sensor (5) which comprises a piezoelectric oscillator (5a). The piezoelectric oscillator (5a) may comprise an AT-quartz crystal (5b) and a metal electrode (5c). A surface capture reagent (5d) is bound to the metal electrode (5c) of the piezoelectric oscillator (5a).

After the target complex (4) is formed under conditions appropriate to the specific elements chosen, the target complex (4) is bound to the sensor (5) under appropriate conditions to form an assay system (6). A signal generating substrate (S) specific for the enzyme (E) is added to the assay system (6) and is converted to a signal generating product (P) which adheres to the surface of the metal electrode (5c) of the sensor (5). The adsorption of the signal generating product (P) alters the resonance frequency of the piezoelectric oscillator (5a) in relation to the change in mass on its surface. The change in resonant frequency is measured electronically.

Figure 2:
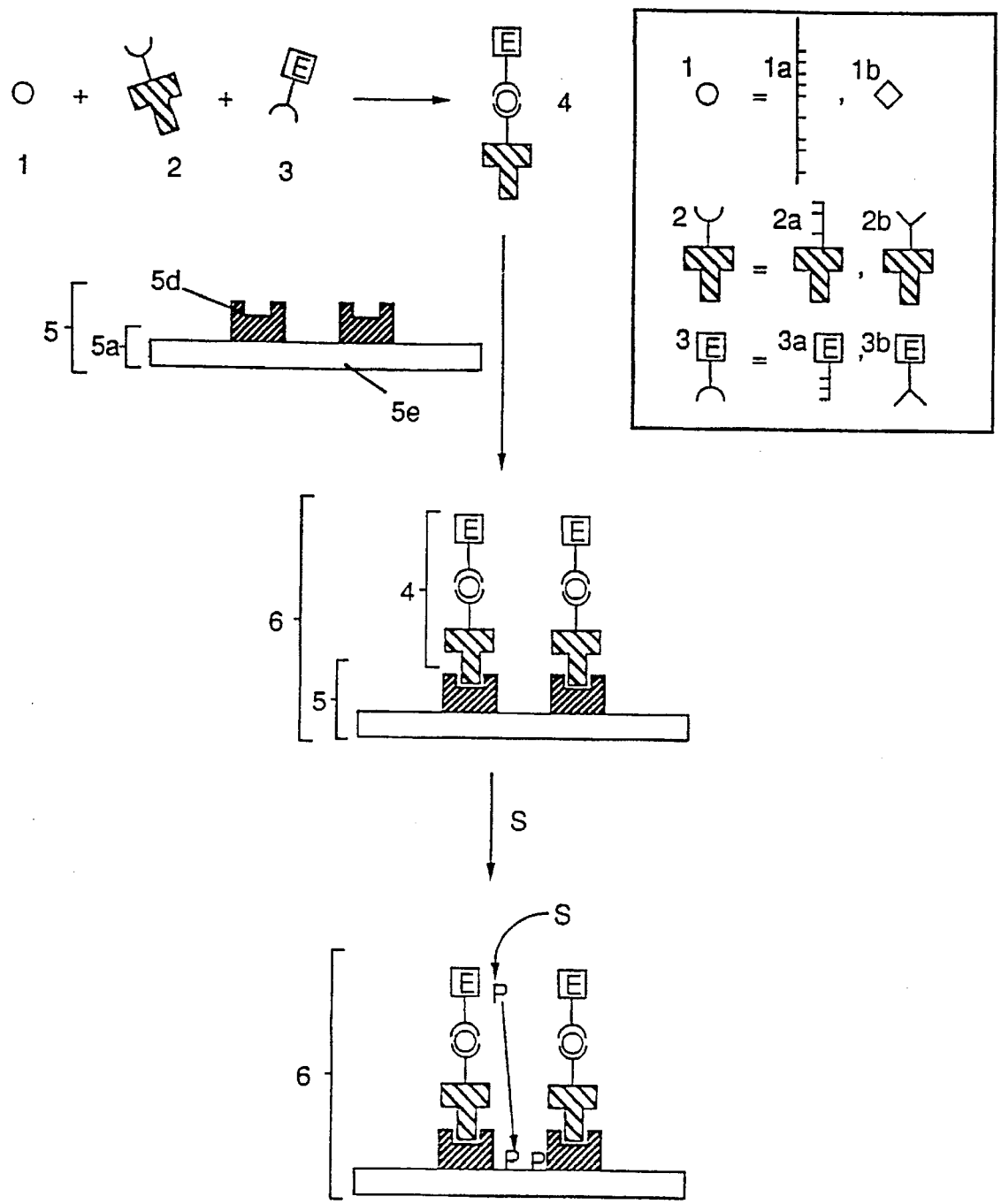
FIG. 2 is a schematic drawing showing the elements and operation of the invention in which the surface capture reagent is immobilized directly onto an optical sensor.

FIG. 2 schematically illustrates the operation of another embodiment of Applicants' invention. In this embodiment the surface capture reagent (5c) is immobilized directly on the surface of the optical sensor (5). The signal generating product (P) is absorbed onto the support surface (5e).

Oligonucleotide Capture Ligands

The oligonucleotide capture ligands must be oligonucleotides containing sequences of base pairs complementary to unique regions of the target analyte.

In most cases, the sequences of the capture ligands in the enzyme reporter conjugate and the bifunctional binder conjugate will have distinctly different gene sequence reactivity. However, in cases where multiple copies of the same gene sequence are contained within the same strand of nucleic acid target the sequences of the two reagents can be identical.

There are several important factors concerning the capture ligands and their preparation which must be considered in order to practice this invention. These considerations include the nature of the sequences in the nucleic acid target and also the binding chemistry of the reagents.

Another important consideration is the length of the oligonucleotide sequence. In general, the nucleotide sequence should be long enough to impart specificity, but not so long as to introduce problems in manufacture or elsewhere. It is generally accepted that the preferred number of base pair sequences needed to impart acceptable specificity is between about 18 and 200 nucleotides. Capture ligands containing less than 60 bases are most easily prepared synthetically using automated DNA synthesizers and are therefore preferred. However capture ligands of up to 25,000 bases can be prepared biosynthetically using cloning techniques known in the art. (Maniatis et al., "Molecular Cloning: A Laboratory Manual", Cold Spring Harbor publisher, 1986, Cold Spring Harbor, N.Y.)

It is further essential that the capture ligand sequences of the enzyme reporter conjugate and the bifunctional binder conjugate be selected so as to be complementary to the same strand of the nucleic acid target. Capture ligands directed toward sequences residing on different complementary strands of the target will not not provide the appropriate detection readout response.

The spatial separation of the reactive sites on the nucleic acid target can be an important consideration in selecting the target sequences for capture ligand construction. In general, the linkage between the sequences that the two capture ligands are directed against should be sufficiently separated and flexible to permit good reactivity with both capture ligands and thus facilitate detection. If the distance is too short, complication with one capture ligand can sterically obstruct access of the other capture ligand. Sequences separated by greater than 5 bases are preferable. The intervening distance provided by this amount of separation of the two sequences to be complexed to the two separate capture ligand sequences is sufficient to enable unobstructed reactivity of both capture ligands and the nucleic acid target analyte.

It is also desirable for this application that the capture ligands of the enzyme reporter conjugate and the bifunctional binder conjugate be non-complementary with each other. Otherwise, cross-hybridization between the capture reagents would produce false positive results.

It is preferable to purify polynucleotide capture ligands prior to the preparation of the two assay conjugates. Methods of isolation and purification of the polynucleotides from cell culture media and synthetic reaction mixtures are well known. Depending on the size and strand structure, the purification can make use of solvent extractions, chromatographic procedures or electrophoretic separations.

While polynucleotides from either a biosynthetic or natural source can be used to prepare the capture ligands to be conjugated to the enzyme and first binder, polynucleotides from a synthetic source are preferred. Synthetic polynucleotides can be made containing nucleotides which have been chemically modified to incorporate linker arms in predetermined positions in the nucleic acid [Ruth et al., DNA, 4, 93 (1985)].

Preparation of Nucleic Acids for Use as Capture Ligands

The nucleic acid sequences useful in the present invention may be any sequence capable of hybridizing with a complementary base sequence. The polynucleotide sequences previously developed or known are therefore applicable.

The methods of preparing polynucleic acids and incorporating various labels such as haptens, enzymes and fluorescent markers is now well established in the art. Sequences can be developed by any suitable means. It is therefore not the intent of this application to teach or improve upon these methods. However, for sake of illustration, nucleic acid sequences could be synthesized with sequences complementary to separate and distinct regions of, for example, a known portion of the HSV-1 gene sequence (D. J. McGeoch et al., *J. Gen. Virol.*, 69, 1531–1574 (1988) and *J. Mol. Biology*, 181, 1–13 (1985)). Sequences could be prepared using an Applied Biosystems, Inc. model 380B DNA synthesizer using standard phorsphoramidite coupling chemistry. In each of the binder and reporter nucleic acids, one of the thymidine derivatives in the sequence would be replaced with a thymidine derivative substituted with a linker arm at the C5 positions as described by Ruth et al. [DNA 4, 93 (1985)]. This modified base substitution would provide the sites for linking the biotin ligand or enzyme reporter to the nucleic acid.

Various methods for attachment of the enzyme reporters and binder ligands to oligonucleotides are now well established in the art and can be used to practice the Applicants' invention. For example, alkaline phosphatase has been directly attached to oligonucleotides by several methods. E. Jablouski et al., *Nucleic Acids Res.*, 14, 6115–6128 (1986), P. Li et al., *Nucleic Acids Res.*, 15, 5275–5287 (1987) attached alkaline phosphatase using a linker-modified nucelotide analog which replaced one of the standard bases in the synthesis of the oligonucleotide. S. S. Ghosh et al., *Analytical Biochemistry*, 178, 43–51 (1989) have reported a second approach in which enzyme is coupled directly to the oligonucleotide derivatized at the 5' end. The alkaline pohsphatase and biotin could be coupled to the respective oligonucleotide probes using the methods of E. Jablouski and P. Li in which the linker-modified nucelotides (At) are functionalized at the terminal amine groups respectively by an -hydroxsuccinimide activated enzyme or biotin moiety. Additional guidance in the synthesis of polynucleotides is found in B. Chu et al., Nucleic Acids Research, 16, 671–3691 (1988); P. Langer et al., Proc. Nat'l. Acad. Sci. U.S.A., 78, 6633–6637) 1081); and A. Alves et al., Nucelic Acids Research, 16, 8722 (1988).

Alternative Capture Ligands

There are two types of capture ligands which can be used to advantage with this piezoelectric assay. These can be distinguished based on the nature of the enzyme reporter conjugate interaction with the target analyte. As described above, the enzyme reporter conjugate can bind with the target by means of hybridization processes in which complementary base sequences on the target and enzyme reporter conjugate associate to form a duplex. Alternatively, target analyte recognition and first capture iigand attachment can be achieved by means of antibody/antigen interactions. In the latter case, the enzyme is attached to an antibody which is specifically directed against the target analyte, e.g., nucleic acid. It is inherent in this type of reaction that the antibody reaction can be directed toward specific molecular features on the target analyte or directed toward a specific region of nucleic acid duplex strands. These duplex regions can be formed by self-hybridization of the target analyte, or involve hybridization of different strands. The duplex regions can be of the DNA/DNA, RNA/RNA, or DNA/RNA types.

Regardless of nature of the target analyte recognition, the enzyme reporter conjugate must contain an appropriate signal generating molecule. Particularly useful are enzymes which are capable of reacting with a substrate to produce an insoluble product or produce a product that insolubilizes a secondary reagent, for example. Non-limiting examples of these enzymes include alkaline phosphate, $\beta$-galactosidase, horseradish peroxidase, urease and glucose oxidase.

Bifunctional Binders

Bifunctional binder conjugates comprise a second capture ligand capable of complementary binding to a target analyte and a binder capable of complexing to a surface capture reagent that is immobilized on the surface of the piezoelectric oscillator. Non-limiting examples of the binder portion of the bifunctional binder conjugate are biotin and iminobiotin. The second capture ligand portion can include nucleic acids, antibodies, lectins, receptors, binding proteins, or chelating agents. The surface capture reagent must be strongly immobilized on the surface of the piezoelectric oscillator, and is capable of forming a complex with the binder portion of the bifunctional binder conjugate. Non-limiting examples of surface capture reagents are antibodies, lectins and other proteins such as avidin and streptavidin.

Alternate Capture Reagents

Another technical improvement which can provide a wider application of the Applicants' method is the use of an antibody bifunctional binder conjugate with the piezoelectric device.

For example, in format designed for hybridization assays, a nucleic acid reporter conjugate is annealed with a target analyte in solution. The specific hybrids are separated from the irrelevant nucleic acids and bound to the piezoelectric sensor using an immunoreaction. In this approach, biotinylated antibodies to nucleic acid hybrids or DNA/RNA hertereopolymers are captured on an avidin coated piezoelectric sensor by the biotin-avidin reaction. The antibody of the bifunctional conjugate may recognize the helical conformation or a unique structural features of the hybrid. For the sake of illustration, antibodies to DNA/RNA have been prepared, Miller, C. A., Patterson, W. L. Johnson, P. K., Swartzell, C. T. Wogeman, F. Albarella, J. P., and Carrico, R. J. (1988), *J. Clin. Microbiology*, 26, 1271–1276.

In an alternative format which does not rely on hybridization reactions for target recognition, a target analyte is first equilibrated with an antibody reporter conjugate. The resulting complex is then removed from nonspecific targets by reaction with a biotinylated antibody binder conjugate and capture of the target complex on the piezoelectric sensor. This is accomplished by reaction of biotin with avidin immobilized on the surface of the piezoelectric oscillator.

Linking Enzymes and Binders to Capture Ligands

A variety of methods can be used to link a modified nucleic acid containing linker arms to an enzyme. Linking agents of the hetero- and homobifunctional types including glutaraldehyde, N,N'-o-phylenedimaleimide, N,N'-oxydimetylenedimaleimide, N-succinimidyl 4-(N-maleimidomethyl) cyclhexane-1-carboxylate, N-succinimidyl m-maleimidobenzoate, N-succinimidyl 3-(2-pyridyldithio)propionate, methyl 3-(4-dithiopyridyl) propionimidate, and N-succinimidyl iodoacetate can be utilized. The linking agents can contain spacer segments of various lengths to permit optimization of nucleic acid attachment. Noncovalent bonding of the enzymes or first binder moieties can also be used. An example of the antigen/antibody complex is the reaction of as arabinonucleic acid and anti-arabinose antibody conjugates (U.S. Pat. No. 4,760, 017, Application Ser. No. 812,514, filed Dec. 23, 1985.) Other types of receptor/ligand complexes potentially could be employed including antibody/antigen complexes, protein receptors, and lectin/carbohydrate interactions. Generally, however, linking chemistry producing non-charged linker spacer arms is preferred. Such linkages minimize nonspecific interactions between target nucleic acids and competing proteins resulting from hydrophobic and/or ionic reactions.

The length of the linker arm on the enzyme moiety of the enzyme reporter conjugate and the bifunctional binder conjugate can be an important factor in providing appropriate reactivity of the first binder moiety or the enzyme moiety of the respective conjugates. Linker arms which are too short can reduce assay efficiency due to steric hindrance of the first binder moiety of the bifunctional binder conjugate binding to the surface capture reagent moiety on the piezoelectric sensor. Short linker arms can also reduce hybridization efficiency between the polynucleotide capture ligand and the nucleic acid target analyte. Generally spacer arms ranging from 4 to 50 carbon units are preferred.

Hybridization Conditions

In carrying out the assay of this invention, careful consideration needs to be given to the conditions in which the nucleic acid target analyte is reacted with the bifunctional binder conjugate and the enzyme reporter conjugate. Since hybridization rates depend on random collisions between the complementary nucleic acid strands, conditions influencing frequency, the effectiveness of the collisions, and the stability of the resulting target complex must be chosen with care. Other factors to be carefully controlled include the concentration of the capture ligands, the temperature, and the assay milieu.

High concentrations of capture reagents can increase the rate of hybridization, but also increase the incidence of non-specific responses by the assay. It is preferable to carry out the hybridization reaction of Applicants' invention using concentrations of the bifunctional binder conjugate and the enzyme reporter conjugate in the range between about $10^6$ and $10^{15}$ copies/mL of the two reagents. More preferred concentrations of the capture reagents are in the range between $10^{11}$ and $10^{13}$ copies/mL. To minimize the nonspecific responses, it is preferable to use the enzyme reporter conjugate in concentrations of 5 to 10 fold less concentration than the bifunctional binder conjugate. Furthermore, the maximum number of bifunctional binder conjugates is limited by the number of available surface capture reagent sites on the piezoelectric oscillator. For example, if the number of bifunctional binder conjugates greatly exceeds the available surface capture reagent sites on the piezoelectric oscillator, binding of the target complex is reduced because of competition from the large excess of bifunctional binder conjugate for the limited number of sites on the surface of the piezoelectric detector. The number of surface capture reagent sites on the piezoelectric oscillator should therefore exceed the number of available bifunctional binder conjugates. Preferably, the binding capacity of the piezoelectric sensor should exceed the amount of bifunctional binder conjugate by 10 to 1000 fold.

Hybridization reactions are temperature dependent because the melt temperature of the duplex strands varies with its nucleotide composition and strand length. For this reason, there is an optimum temperature to carry out the hybridization phase for each assay. In general, a temperature approximately 25° C. below the lowest melt temperature of the target analyte can be used. The preferred temperature range is generally between 25° C. and 37° C.

Salt (Na ion) concentration may also affect the rate of hybridization and, therefore, optimum salt concentrations can vary for different assays. Generally, sodium ion concentrations in the range of 0.3 to 2.0M are preferred. Divalent cations which can be found as impurities in many reagents can also lower hybridization rates. To rid solutions of divalent cations, it may be necessary to include a chelator such as EDTA in the assay milieu.

Samples to be Assayed

The samples to be assayed can be obtained from many different types of materials. Usually, they will be of medical, veterinary, environmental or industrial significance and be derived from human and animal specimens, body fluids and exudates. For example, the materials may be urine, blood, milk, cerebrospinal fluid, sputum, fecal matter, lung aspirates, throats swabs, genital swabs, rectal swabs and nasopharangal aspirates.

The nucleic acids for analysis in these types of samples are frequently contained within cells and may be complexed with other biopolymers such as proteins and carbohydrates. The nucleic acids may be composed of RNA or DNA and may be of either single or double stranded forms. In most cases, the nucleic acids must be released from the cells or biopolymer complex and prepared in a form suitable for analysis.

Target Nucleic Acid Preparation

Both single stranded and double stranded nucleic acids can be analyzed by the method of this invention. In cases where the analysis is for a specific gene sequence, the nucleic acids must be in a single stranded form in order to complex with the capture ligands. Samples containing double stranded nucleic acids must therefore be denatured and maintained in a single stranded form prior to analysis. In some instances, single-stranded nucleic acid samples must also be denatured if they are coiled or contain regions of self-hybridizations.

Many approaches for denaturing the nucleic acids are well known by those skilled in the art (T. Maniatis, E. F. Fritsch and J. Sambrook, "Molecular Cloning", Cold Spring Harbor Laboratory, (1982)). Generally, denaturation can be accomplished by heating in boiling water or alkali (e.g. 0.1N sodium hydroxide). Applicants have found that one way denaturation can be accomplished is by boiling the target nucleic acid in purified water for 10 min. The sample is then chilled rapidly in ice for at least 2 min. and then maintained in ice prior to analysis for periods of less than one hour.

In some cases the denaturation process can be used to simultaneously lyse cells and release the nucleic acids from biopolymers. After denaturation, it may be desirable to centrifuge the sample at 4° C. to remove sample debris. If the target analyte is RNA, alkali denaturation should not be used because this condition degrades RNA.

Release of nucleic acids can also be accomplished by physical disruption (including freeze/thaw, abrasion, sonication), chemical disruption (including detergents such as Triton®, Tween®, sodium dodecylsulfate), osmotic shock, and enzymatic lysis (including enzymes such as lysozyme, proteinase K, pepsin). Once in a single-stranded form the nucleic acids can be assayed according to the present hybridization method.

During the denaturation process some fragmentation of the target analyte may occur as a result of mechanical shearing and chemical cleavage. Some fragmentation can be advantageous since shorter targets tend to react faster because of faster diffusion rates and reduce the strength of nonspecific hybridization processes. While not intending to be limiting, target analytes ranging from 50 to 2000 bases are preferable. For this reason it may be desirable to first fragment the target at specific base sequence sites using restriction enzymes. However, too much fragmentation can be detrimental to assay response if the chains are fragmented in pieces so small that the enzyme reporter conjugate and bifunctional binder conjugate hybridization sites are not maintained on the same fragment. Fragmentation can also be damaging if one or the other capture ligand hybridization sites is altered.

Assay Conditions

While optimum hybridization conditions vary according to the nature of the specific reagents and target analytes as described above, it is desirable to select hybridization conditions which can be used with different target analytes. The hybridization of single stranded target nucleic acids with the bifunctional binder conjugate and enzyme reporter conjugate can be accomplished in an aqueous hybridization milieu consisting of, as a non-limiting example: (a) from 3 to 8 fold SSC buffer at pH 7.0, preferably 4.8 to 6 fold SSC; (b) 0.1 to 1.5% (w/v) the quaternary ammonium detergent Triton® X-100, preferably from 0.8 to 1.33% (wt./v) Triton X-100; (c) deionized formamide from 5 to 25% (v/v), preferably from 8 to 15% (v/v) formamide. Hybridization at higher formamide concentrations up to 70% can also be achieved. However, it is well known that the rate of hybridizations at higher formamide concentration are slower (Casey et al., Nucleic Acids Research, 4, 1539 (1977)). Furthermore, exposure of enzyme reporter conjugate to high concentrations of formamide can damage the activity of the enzymes. Formamide can be deionized using Dowex XG8 mixed-bed resin. (c) 0.5 to 1.0% (wt./v) bovine serum albumin (BSA), preferably from 0.5 to 0.2% (wt./v) BSA.

It is desirable that the kinetics of the hybridization and binding of the target complex to the surface capture reagent be rapid reactions in order to shorten the assay time. While it is difficult to predict the kinetics of the hybridization process, partly because the exact concentrations of target analyte and capture reagents are unknown, rapid responses can be achieved by using excess bifunctional binder conjugate and enzyme reporter conjugate reagent concentrations and by performing the assay at elevated temperatures, preferably from 25° to 37° C. Under these conditions, hybridization of the capture reagents with the target analyte and binding of the resulting target complex to the surface capture reagent can be accomplished in 10 to 60 minutes.

The concentrations of the capture reagents not only directly affect the rates of hybridization and the rate of binding of the target complex to the surface capture reagent on the piezoelectric oscillator, but also affect the sensitivity of the assay. For these reasons, the concentrations of the two capture reagents are maintained at high concentrations exceeding the target analyte concentrations. As stated previously, too high a reagent concentration can diminish assay reliability through nonspecific binding of the enzyme reporter conjugate to the piezoelectric detector.

To increase the speed of the reaction and the efficient use of reagents, it is desirable to perform the hybridization in as small a volume as possible. Under these conditions the kinetics of nucleic acid reassociation are faster and the amount of reagents needed to drive the reactions are reduced.

In certain instances it can be a further advantage to perform the hybridization under different conditions than those used to bind the target complex to the piezoelectric sensor. For example, with larger target strands requiring more stringent conditions to avoid nonspecific hybridization, it can be useful to run the hybridization at a higher temperature than that used to bind the target complex to the surface of the piezoelectric sensor. Different concentrations of formamide or salt may be useful as well. This can be accomplished by performing the assay in separate stages. The hybridization can be performed in the first stage under one set of conditions. The conditions then can be readjusted to carry out the binding of the target complex to the piezoelectric sensor. It is, therefore, an inherent advantage of Applicants' invention that the hybridization and the binding of the target complex to the piezoelectric sensor can be performed either simultaneously or sequentially in stages without reagent interference or compromising assay response.

The assay is completed by introducing a small amount of solution containing the hybridized target complex to the piezoelectric sensor and incubating the complex with the surface capture reagent for an appropriate time period to permit target complex to bind to all of the available surface capture reagent. The piezoelectric sensor is then washed to remove any non-specifically bound enzyme reporter and buffer solution is added so that the piezoelectric sensor, onto which the target complex is immobilized, is immersed in solution. Then a signal generating substrate is introduced to the solution and the accumulation of the signal generating product measured electronically by the frequency change of the piezoelectric oscillator.

Non-hybridization assays, such as immunoassays, can be performed using essentially the same procedural steps described above for hybridization assays. However, the hybridization reaction conditions may not be optimal for an immunoassay. Generally, it is desirable for immunoassays to perform the reaction at room temperature and not to use formamide or other denaturing reagents when carrying out the equilibration of the target analyte with the enzyme reporter and bifunctional binder conjugates. The buffers used in this step should be selected to favor both the immunological and enzymatic reactions and prevent nonspecific interactions of the reporter or target to the sensor surface. We have found that buffer compositions containing 50 mM Tris buffer pH 7.4, and 0.1% to 1.0% bovine serum albumin (BSA) can be used for this step of the assay. In some instances, addition of 0.1% Poly-Tergent SL-18 detergent (Olin Chemicals, Stamford, Conn.) can be useful in suppressing non-specific binding. For specific applications, alternative buffer compositions used in solid phase enzyme immunoassays may also be useful. The composition of three of the most generally used buffers are described in "The Theory and Practice of Enzyme Immunoassays", P. Tijssen, page 331, Elsevier, New York, N.Y. (1985).

Piezoelectric Sensor

The piezoelectric sensor comprises the piezoelectric oscillator with its electrode surface and the surface capture reagent on the surface of the electrode. The piezoelectric oscillator can be fabricated from shear mode piezoelectric crystals such as AT-cut quartz, surface acoustic wave materials such as ST-cut quartz or flexural mode plates such as zinc oxide films on silicon nitride wafers.

Oscillators using AT-cut quartz consist of a single crystal wafer sandwiched between two electrodes and often referred to as a quartz crystal microbalance (QCM). The electrodes are provided with means for connection to an external oscillator circuit that drives the quartz crystal at its resonant frequency. This frequency is dependent on the mass of the crystal, as well as on the mass of any layers confined to the electrode areas of the crystal. Thus, the frequency is altered by changes in mass on the surface of the electrodes or in any layers on those electrodes. In general, the change in resonant frequency of these devices can be correlated to the amount of mass change. If the QCM and any attached layers obey rigid-layer behavior, the mass changes are determined from the shift in the resonant frequency according to the Sauerbrey relationship.

Surface acoustic wave (SAW) devices are also applicable to this invention. These devices comprise interdigitated microelectrode arrays on the surface of a piezoelectric quartz substrate. They exhibit frequency changes that can be correlated with mass changes at their surface arising from changes in the, velocity of a transverse surface wave. Flexural plate-mode devices are also capable of measuring mass changes at the surface of a piezoelectric substrate.

The electrode surface which is most germane to shear mode oscillators may comprise one of several metals including gold, silver, aluminum, copper and silicon. The surface capture reagent possesses binding sites that are complementary to those of the bifunctional binder conjugate, and may belong to the general class of binding proteins such as avidin, streptavidin, iminobiotin and antibodies (both monoclonal and polyclonal in origin).

Immobilization of the surface capture reagent to the electrode surface can be accomplished by directly adsorbing the surface capture reagent to a receptive surface such as gold. An alternative approach is to react the surface capture reagent with the electrode surface that has been modified previously with attached reagents possessing linker arms capable of attaching to the surface capture reagent by either covalent, ionic or immunological interactions. These reagents may include those that attach to the electrode surface by covalent attachment such as silane reagents, or reagents that are strongly adsorbed to the electrode surface such as thiols and disulfide compounds. The alkyl trichlorosilane reagents, the thiol reagents, and disulfide reagents may be terminated with functional groups capable of reacting with the surface capture reagent. These functional groups are known collectively as "adhesion promoters." An "adhesion promoter" refers to a reagent having at least one functional group capable of reacting with the surface capture reagent and at least one functional group capable of reacting with the surface of the transducing element of the biosensor. In Applicants' invention, the transducing element of the biosensor is, for example, either a piezoelectric oscillator or an optical sensor surface.

The linker arms contained in these reagents may be any of several, including those described above in the section entitled "Linking Enzymes and Binders to Capture Ligands". For example, the general class of aminosilanes, when attached to the piezoelectric oscillator surface via M-O-Si linkages, can be used to immobilize the surface capture reagent by covalent linkage between the nitrogen atom of the aminosilane and an appropriate functional group on the surface capture reagent. Alternatively, the surface capture reagent can be immobilized by adsorption onto polymer layers, monolayer films, or the metal electrode surfaces themselves. A non-limiting list of metals includes gold, silver, copper, aluminum, and silicon. Other useful surfaces are polymer films and silane reagents that serve to enhance the binding of the surface capture reagent by either hydrophobic interactions. An example of a polymer film is polystyrene, which itself can be applied by spin coating. Higher surface area coatings for greater coverages of surface capture reagent can be achieved by fabrication of irregular and three dimensionally shaped surfaces, such as by aerosol application which deposits minute droplets of polymer. Suitable silanes include the general class of alkyl trichlorosilanes, which covalently bind to the metal electrode surfaces of the piezoelectric oscillator by M-O-Si bonds.

Optical Sensor

The surface capture reagents can be immobilized onto the optical sensor surfaces by similar means, either by adsorption directly on the optic element or onto coatings applied thereto, or by covalent attachment to linkages covalently attached to the optic element. Suitable reagents and adhesion promoters include those described above for piezoelectric oscillators.

Separation of Uncaptured Materials

In the operation of Applicants' invention, the enzyme reporter conjugate and bifunctional binder conjugate are used in excess. It is therefore important, following the capture of the target complex, that the sensor be freed of excess conjugate reagents not specifically bound to the surface of the sensor. Failure to remove the unbound conjugate reagents prevents accurate determination of target concentrations. Generally, removal of excess conjugate reagents can be accomplished by first removing the test fluids and then washing the piezoelectric sensor three times with a two-fold excess of wash buffer. Various aqueous buffer/detergent compositions can be used, however, the optimum compositions may vary with the nature of the sample matrix and specific reagents employed in the assay.

The wash fluid used herein consisted of 15 mM sodium citrate, 150 mM sodium chloride, and 0.17% v/v the quaternary ammonium detergent Triton® X-100 detergent.

Signal Generating Substrates and Enzymes

Examples of signal generating substrate systems which are capable of producing insoluble signal generating products which are in turn capable of accumulating on the surface of the piezoelectric oscillator include insoluble dyes. For example, alkaline phosphatase reacts with 5-bromo-4-chloro-3-indolyl-phosphate (BCIP). In this case the enzymatically catalyzed hydrolysis of BCIP produces an insoluble dimer which precipitates on the surface of the piezoelectric oscillator. Other analogous substrates having the phosphate moiety replaced with such hydrolyrically cleavable functionalities as galactose, glucose, fatty acids, fatty acid esters and amino acids can be used with their complementary enzymes to vary the specificity and properties of the reporter enzyme. In this way, practioners can avoid interferences and increase stability.

Other signal generating substrate systems include peroxidase enzymes such as horseradish peroxidase or myeloperoxidase, and one of the following: (a) benzidene dyes such as benzidene dihydochloride, and diaminobenzidine; (b) carbazole dyes such as 3-amino-9-ethylcarbazole; and (c) naphthol dyes such as 4-chloro-1-napthol, all of which have been reported to form precipitates upon reaction with peroxidases. Also, oxidases such as alphahydroxy acid oxidase, glucose oxidase, and xanthine oxidase can be used with oxidizable tetrazolium dye systems such as a phenazine methosulfatenitrobluetetrazolium mixture.

Alternatively, signal generating substrate systems can be used that induce deposition of secondary reagents. For example, urease in the presence of urea can induce deposition of pH sensitive polymers. Particularly useful are amphoteric terpolymers or other pH sensitive polymers comprising acrylic acid, methyl methacrylate and dimethylaminoethylmethacrylate.

The polymer is chosen or designed to react with an enzymatic reaction product via ion pairing, complexation reactions, redox reactions, or covalent coupling.

For example, a pH sensitive amphoteric co- or terpolymers of acrylic acid (AA), alkyl methacrylate (RMA), and N,N-dimethylaminoethyl methacrylate (DMAEMA) polymer can be designed to respond to enzymatically induced changes in pH, whereupon proton neutralization changes the net charge on the polymer and alters the physical properties of the polymer. The isoelectric polymer accumulates on the oscillator as the pH at the sensor surface approaches the isoelectric point of the complex. The isoelectric polymer adsorbs onto the piezoelectric sensor and changes the resonant frequency. The deposit on the piezoelectric oscillator gives a corresponding frequency decrease that can be read electronically to determine the amount of enzymatic activity and thereby the amount of bound target complex.

For example, variations in pH induced by the immobilized urease upon enzymatic conversion of urea to ammonia renders the soluble polymer isoelectric and causes adsorption of the polymer at the piezoelectric oscillator surface.

The polymers are generally soluble in water at all pH's other than their isoelectric points (pI). The isoelectric point is determined by the ratio of acid to base groups and thus can be varied by synthesizing polymers with appropriate ratios. The preferred ratio for polymers used in the instant invention is such that the polymer's pI is in the physiological region. (The pI is necessarily dependent on the pKa values for the component groups.) Responses can also be affected by the nature and size of the neutral, non-ionic segment, which can influence the pK of the component acid and base moieties.

The solubility characteristics of the polymers are strongly influenced by their ion content. Polymers having significant neutral hydrocarbon segments are less water-soluble at their isoelectric point than polymers with little or no neutral segments. Applicants have prepared a series of polymers containing different alkyl methacrylates and having variable segment fractions, all with pI's in the physiological range. Several other polymers having different solubility and associative characteristics are also predicted to be suitable.

The sensitivity of the polymer to small changes in pH is largely dependent on the narrowness of its composition distribution. A narrow composition distribution is generated by controlling the ratio of reacting monomer in the reaction medium. This ratio is not that found in the polymer but is determined by the reactivity ratios of the constituent monomers. The ratio can be maintained by using either a balanced feed or a starved feed reaction process. The balanced feed process described in the U.S. Pat. Nos. 4,735,887 and 4,749,762, herein incorporated by reference, requires careful reaction control, but leads to rapid formation of high molecular weight product. The starved feed process is preferable when rapid production of high molecular weight product is unnecessary. The starved feed process involves the addition of feed monomer at a rate much lower than its bulk reaction rate in neat media. The reaction becomes essentially a living free radical process, occurring only when monomer encounters an emulsion particle containing a living radical. Enough "balance monomer" is added to saturate the aqueous phase (determined as the point where the solution starts to develop translucence), before starting addition of initiator. A slight excess of MA should also be maintained to give the correct product composition. This is easily accomplished because of the favorable relationship between total inherent reaction rate and reactivity ratios for the acrylate-methacrylate system.

Many combinations of monomer are capable of yielding polymers having pI's in the physiological pH range. Amphoteric polymers can be prepared from various combinations of the following sets of monomers set out below:

A. Acidic monomers—Molecular or ionic substance that can yield a hydrogen ion to form a new substance. Examples are acrylic acid, methacrylic acid, and monomers containing phosphoric acid and sulfinic acid groups.

B. Basic monomers—Molecular or ionic substance that can combine with a hydrogen ion to form a new compound. Examples are DMAEMA, diethylaninoethyl methacrylate, t-butylaminoethyl methacrylate, morpholinoethyl methacrylate, piperidinoethyl methacrylate.

C. Neutral monomers—Molecular or ionic substance that is neither acidic or basic. Examples are alkyl methacrylates (MMA, EMA, BMA), hydroxyethyl methacrylate (HEMA), hydroxypropyl methacrylate, vinyl pyrrolidone, vinyl acetate (vinyl alcohol on hydrolysis), arcylamides, vinyl ethers, styrene. (Reaction of co-monomers having vastly differing reactivity ratios requires very careful reaction control and therefore is not preferred.)

In addition, any aqueous-soluble amphoteric polymer with a pI in the physiological range may be useful as a pH sensitive polymer. Specific examples include:

(1) polymers generated by the reaction of dimethylamino ethanol and similar compounds with methylvinylether/ maleic anhydride copolymers; and (2) hydrolyzed copolymers of vinyl pyridine and methyl acrylate.

Still other signal generating polymers can be formed by linking antibodies, polynucleic acids, receptors, chelating agents, cellular adhesion factors, and ligand binders to aqueous soluble polymers containing pendent hydroxyl, carboxyl, amino, thio, aldehyde, anhydride, imide and epoxy groups. In the process, the polymer containing one or more of these pendent groups is reacted with a linking agent to form an intermediate group that is reactive toward the binder or capture reagent.

The resulting polymer reagent will react with the target analyte to form a molecular aggregate. The resulting aggregate produced by crosslinking of the polymer reagent with the target analyte reduces the solubility of the complex as a result of the increase in molecular size. This induces deposition of the polymer complex on the sensor surface.

Thus, the design of a specific signal generating polymer for purposes of this invention is guided by the target complex to which it will complex or react (i.e., $H^+$ or a specific antibody) and by the environmental requirements of the target analyte to be assayed.

Adding Substrate for the Enzyme of the Enzyme Reporter Conjugate

The frequency of the piezoelectric oscillator with bound target complex is measured in buffer solution, and then a standard solution of the substrate is directly added. The rate of frequency change, as well as the total frequency change after a time considered to be the optimum measurement interval, are measured in solution and, since the enzyme reporter conjugate is present only when the target complex is bound to the surface, the rate of frequency change is indicative of the amount of target complex, and therefore target analytes in the sample. Although not the preferred mode, the frequency of the oscillator could also be measured in the dry state before addition of the signal generating substrate and then again after a period of time following addition of the signal generating substrate. The difference in frequency is indicative of the amount of target complex, and therefore target analytes in the sample, bound to the piezoelectric oscillator. The mode of operation could also include the use of a reference piezoelectric oscillator which is exposed to the same solutions but which has not been modified so as to have surface capture reagent immobilized on its surface. The signal generating substrate would then be added and the difference in frequency between the sample and reference crystal measured. This embodiment has the potential advantage of minimizing errors due to viscosity, temperature and non-specific binding. Operation with only the sample crystal, however, is feasible because (1) the viscosity and temperature changes during addition of the substrate and during measurement are not large, (2) interference from non-specific binding is minimized by the washing step and (3) the measurement step poses no risk of mass changes from processes other than those induced by the accumulation of signal generating product at the surface of the piezoelectric sensor. The signal measured is amplified by the large turnover numbers of the enzymatic reaction, which produces concentrations of product far exceeding that of the target complex.

The frequency measurements are made with a conventional oscillator circuit, the design of which is well known to those in the art, and a commercially available frequency meter, coupled with a system for computerized data acquisition. The device can comprise either a single sample well, or a multi-well analysis plate with multiple oscillator circuits, frequency counters, a reagent delivery system and a computer acquisition system. Each circuit may be referenced against its own reference sensor or all sensors of the array may be referenced collectively to a common sensor. The reagent delivery system would incorporate the necessary plumbing and controllers so that samples can be introduced and washing performed automatically.

Optical Detection

The deposition of organic molecules or polymers on the surface of the sensor not only adds mass which facilitates piezoelectric detection, but also alters other physical properties at the interface between the oscillator surface and the surrounding test milieu. These changes could provide an alternate means to measure target analyte concentrations. For example, polymer deposition alters the index of refraction at the sensor surface. These changes could be proportionately related to the concentration of target analyte in the test milieu. As a consequence, enzyme induced polymer deposition could provide a highly sensitive means of optical readout for the test method of the Applicants' invention.

Generally, the index of refraction of synthetic polymers will differ from that of aqueous test media. For example, halogen containing polymers tend to have an index of refraction equal to or less than that of the aqueous test milieu ($\leq 1.36$). If the polymer contains —C(H)$_x$— or —C(CH$_5$)— segments, then the index of refraction tends to be equal to or greater than that of the test milieu ($\geq 1.35$). By utilizing an optical sensor composed of a light conducting material of an appropriately higher index of refraction than either the surrounding test milieu or the indicator polymer, changes in the polymer deposition on the surface of the optical sensor will alter light propagation through the optical sensor matrix. For example, polymer deposition could be used to decouple or alter light propagation through an optical window, planar wave guide or optical fiber. This detection principle used in combination with various light splitting devices, such as a bifurcated optical fiber or machzehnder device, could provide an internal reference which would facilitate detection of changes in light propagation such as wave length, phase, polarization or intensity of the test beam relative to the reference beam. The waveguide provides a large differential optical density between waveguide material (high index of refraction) and the adjacent test fluid (low index of refraction). Under these conditions, light is totally internally reflected within the body of the planar or fibre optic waveguides. A portion of the light is propagated as an evanescent wave in the test medium. This evanescent wave has a characteristic penetration depth of a fraction of a wave length into the aqueous test fluid phase. Optical interaction with substances on the surface exhibiting differences in index of refraction, light scattering or light adsorption can thus alter the propagation of light within the waveguide. By this means, the deposition induced by the reporter/target complex on the surface of the waveguide of polymers or organic materials possessing index of refractions different from the test fluid, can alter the propagation of light in proportion to the concentration of target complex bound.

Alternately, polymer deposition could be detected by means of changes in plasmon resonance, see H. Raether "Surface Plasmons", Springer-Verlag, New York, 1988. Suitable materials for the optical sensor matrix can be inorganic such as fused quartz, potassium doped glass or polymers such as polymethylmethacrylate.

EXAMPLES

The following nonlimiting examples, including the detection of HSV, illustrate the basic principles and unique advantages of the present invention.

EXAMPLE 1

Piezoelectric detection of binding of biotinylated alkaline phosphatase conjugate to avidin coated gold films This example illustrates that the gold electrodes of the QCM can be modified by the addition of a thin layer of avidin. Subsequent exposure of the avidin film to a conjugate consisting of biotin and an enzyme forms a surface complex that can induce the enzymatic conversion of a substrate into a product that accumulates on the QCM surface and results in a measurable frequency change.

A quartz crystal (QCM) was coated with avidin by immersing the QCM in an aqueous pH 7.4 phosphate buffered saline solution (10 mM phosphate, 120 mM sodium chloride, 2.7 mM potassium chloride) containing 1 mg/ml egg white avidin (SIGMA, St. Louis, Mo., Cat. No. A-9300). The QCM are then rocked in the avidin solution for 4 hours at room temperature. The QCM are then freed of excess avidin by washing 4 times with the above phosphate buffered saline solution. Prior to use, the avidin QCM sensors can be stored immersed in the PBS buffer containing 0.5% sodium azide at 4° C.

The crystal was then exposed in 2 mL phosphate buffer solution to a conjugate (750 ng/mL) consisting of biotin and alkaline phosphatase (SIGMA, St. Louis, Mo.). After washing with buffer solution, the crystal was immersed in 0.5 mL 50 mM TRIS buffer solution and, while monitoring the frequency, 0.5 mL of 5-bromo-4-chloroindolylphosphate solution (BCIP, from SIGMA, St. Louis, Mo.) was added. The change in frequency with time, dΔf/dt, and the overall frequency decrease were indicative of deposition onto the crystal of the oxidized dimer of the BCIP substrate that follows enzymatic hydrolysis of the substrate (Table 1).

TABLE 1

| Example | initial dΔf/dt (Hz/min) | Δf after 10 min. (Hz) |
|---|---|---|
| 1 | 306 | 1050 |

EXAMPLE 2

Piezoelectric detection of binding of biotinylated alkaline phosphatase conjugate to streptavidin coated gold films This example illustrates that the gold electrodes of the QCM can be coated with streptavidin. Subsequent exposure of the streptavidin film to a conjugate consisting of biotin and an enzyme forms a surface complex that can induce the enzymatic conversion of a substrate into a product that accumulates on the QCM surface and results in a measurable frequency change.

A QCM crystal was incubated with 200 µg/ml streptavidin in 2 mL phosphate buffer solution 200 µg/mL for three hours. Excess streptavidin was then removed by washing with buffer solution. The crystal was then exposed in 2 mL phosphate buffer solution to a conjugate (750 ng/mn) consisting of biotin and alkaline phosphatase (SIGMA, St. Louis, Mo.). After washing with buffer solution, the crystal was immersed in 0.5 mL 50 mM TRIS buffer solution and, while monitoring the frequency, 0.5 mL of 5-bromo-4-chloroindolylphosphate solution (BCIP, from SIGMA, St. Louis, Mo.) was added. The change in frequency with time, dΔf/dt, and the overall frequency decrease were indicative of deposition of the oxidized dimer of the BCIP substrate due to the enzymatic hydrolysis of the substrate (Table 2).

TABLE 2

QCM responses after BCIP addition to streptavidin films that have been exposed to different concentrations of biotin and treated with biotin/alkaline phosphatase-reporter conjugate.

| Example | initial dΔf/dt (Hz/min) | Δf after 10 min. (Hz) |
|---|---|---|
| 2 | 280 | 1020 |

EXAMPLE 3

Piezoelectric determination of temperature effects on enzymatic reaction rates

This example illustrates that the frequency response associated with an enzymatic reaction is dependent upon temperature during BCIP addition to a QCM modified with a conjugate consisting of biotin and an enzyme bound to the surface complex of avidin.

Crystals were incubated with avidin (SIGMA, St. Louis, Mo.) in 2 mL phosphate buffer solution (200 ug/mL) for three hours, followed by washing with buffer solution. The crystals were then exposed in 2 mL phosphate buffer solution to a conjugate (750 ng/mL) consisting of biotin and alkaline phosphatase (SIGMA, St. Louis, Mo.). After washing with buffer solution, the crystals were individually immersed in 0.5 mL 50 mM TRIS buffer solution at either 25° C. or 37° C. While monitoring the frequency, 0.5 mL of 5-bromo-4-chloroindolyl-phosphate solution (BCIP, from SIGMA, St. Louis, Mo.) was added. The change in frequency with time, dΔf/dt, and the overall frequency decrease were indicative of deposition of the oxidized dimer of the BCIP substrate that follows enzymatic hydrolysis of the substrate (Table 1). Comparison of dΔf/dt and the overall frequency change at the two temperatures indicated faster enzymatic reaction rates at 37° C., as expected (Table 3).

TABLE 3

| Example | initial dΔf/dt (Hz/min) | Δf after 10 min. (Hz) |
|---|---|---|
| 3 (25° C.) | 300 | 1010 |
| 3 (37° C.) | 360 | 2000 |

EXAMPLE 4

Modulation of frequency response due to competitive binding of biotin to avidin coated gold films This example illustrates that the response observed in Examples 1–3 is due to the binding of the biotin-alkaline phosphatase conjugate to the avidin (or streptavidin) which has been adsorbed to the surface of the crystals and that the resulting response of the crystal can be modulated by the number of available binding sites, as determined by competition with biotin.

Figure 3:
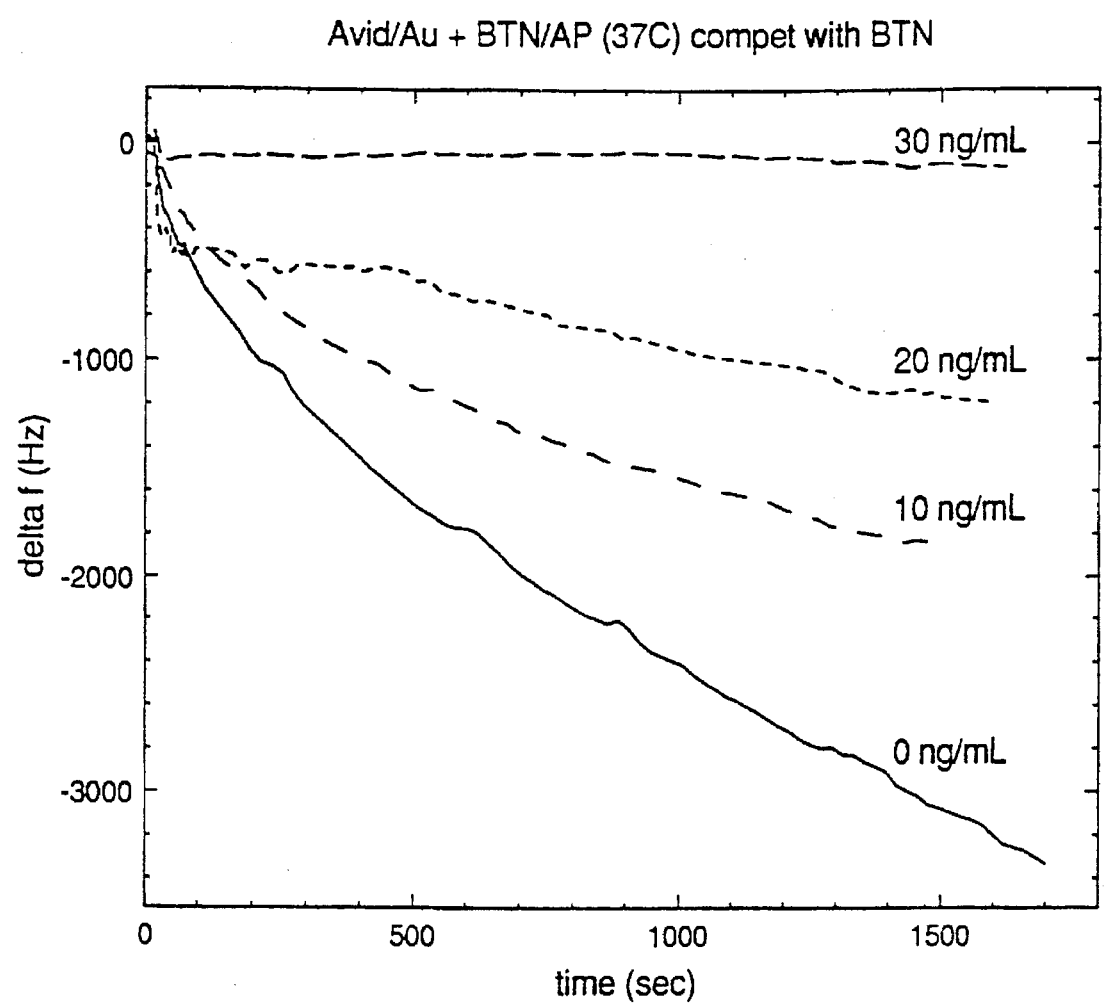
FIG. 3 is a graph showing the frequency response due to BCIP dimer deposition in competition with varying amounts of unlabeled biotin.

Crystals were incubated with avidin (SIGMA, St. Louis, Mo.) in 2 mL phosphate buffer solution (200 ug/mL) for three hours, followed by washing with buffer solution. The crystals were then exposed in 2 mL phosphate buffer solution to varying amounts of biotin (SIGMA, St. Louis, Mo.) in the range 0–30 ng/mL for 15 minutes. After washing with buffer solution, the crystals were then exposed in 2 mL phosphate buffer solution to a conjugate (750 ng/mL) consisting of biotin and alkaline phosphatase (SIGMA, St. Louis, Mo.). After washing, each crystal was individually immersed in 0.5 mL 50 mM TRIS buffer solution and, while monitoring the frequency, 0.5 mL of 5-bromo-4-chloroindolylphosphate solution (SIGMA, St. Louis, Mo.) was added. Larger concentrations of biotin resulted in smaller frequency responses owing to lesser amounts of conjugate reagent binding to the avidin films, in accord with competition for the avidin binding sites by biotin (Table 4 and FIG. 3).

TABLE 4

QCM responses after BCIP addition to avidin films that have been exposed to different concentrations of biotin followed by the addition of biotin-alkaline phosphatase conjugate.

| Biotin concentration ng/mL | nmol/mL | dΔf/dt (Hz//min) | Δf after 10 min. |
|---|---|---|---|
| 0 | 0 | −287 | −1800 |
| 10 | 41 | −250 | −1150 |
| 20 | 83 | −27 | −700 |
| 30 | 124 | 0 | 0 |

EXAMPLE 5

Detection of a DNA target strand

This example illustrates that single stranded DNA in a sample could be detected by prior hybridization of the target analyte with a bifunctional binder conjugate comprising biotin linked to a complementary oligonucleotide and a conjugate comprising an enzyme reporter linked to a complementary oligonucleotide. The target complex could then be captured via the biotin on an avidin film previously immobilized on the piezoelectric oscillator. The enzymatic conversion of a substrate into a product that accumulates on the piezoelectric oscillator surface was achieved by addition of the alkaline phosphatase enzyme reporter conjugate resulting in a measurable frequency change.

Prior to testing, a hybridization buffer could be prepared by mixing 6.0 mL of 20 X SSC buffer (pH 7.0), with 0.2 mL the quaternary ammonium detergent Triton® X-100 detergent (SIGMA, St. Louis, Mo.), 2.0 mL deionized formamide, 0.025 mL 1N hydrochloric acid in 12.8 mL of purified water. This buffer would be stored at $-20°$ C. Just before use, the hybridization buffer would be thawed and used to prepare a hybridization test milieu containing 0.5 mL of the hybridization buffer, 0.010 mL of an aqueous solution containing alkaline phosphatase free bovine serum albumin (50 mg/mL), 0.02 mL of a solution (ca. 11 ng/mL) containing a bifunctional binder reagent ($10^{11}$–$10^{12}$ copies) comprising biotin covalently linked to a synthetic oligonucleotide with a sequence complementary to a separate and distinct region of the target analyte, and 0.010 mL of an aqueous solution (ca. 1 ng/mL) of an enzyme reporter conjugate ($10^{11}$–$10^{12}$ copies) prepared with a synthetic oligonucleotide sequence complementary to a second region of the target analyte.

The synthetic oligonucleotides contained in the bifunctional binder conjugate and the enzyme reporter conjugate each possess between 18 and 200 nucleotides. The regions in the target analyte complementary to the respective sequences in the bifunctional binder conjugate and the enzyme reporter conjugate preferably are separated by greater than five nucleotides. Insertion of the binder arms into the polynucleotide capture ligands may be accomplished with techniques incorporated by reference above in the specification sections entitled "Preparation of Nucleic Acids" and "Linking Enzymes and Binders to Capture Ligands."

Concentrations of the enzyme reporter conjugate and the bifunctional binder conjugate are dependent upon the expected concentration of the target analyte to be detected. The enzyme reporter conjugate should be used in concentrations 5 to 10 fold times less than the concentration of the bifunctional binder conjugate. Furthermore, the number of available surface capture reagent binding sites on the piezoelectric oscillator should exceed the number of bifunctional binder conjugates by 10 to 1000 fold.

A sample (0.010 mL) containing a single stranded target analyte would be first denatured by mixing with 0.03 mL of purified water and then heating the solution in boiling water for 10 min. The stock target solution would be then quickly chilled in an ice bath for at least 2 min and then centrifuged at 3000 g for 3 min. Dilution of the stock target solution could be performed to prepare test samples containing lower concentrations of the target.

For testing, 20 µl portions of the denatured target samples would then be added to 0.5 mL of the above hybridization test milieu. The reaction mixture would then be then incubated at 37° C. for 20 min. Following the hybridization step, the reaction mixture would then be brought to room temperature (ca. 25° C.) and transferred to the piezoelectric sensor to capture the target complex. After equilibrating for 15 min, the test fluid would be removed, the quartz crystal washed three times with SSC wash buffer solution containing 15 mM sodium citrate, 150 mM sodium chloride, and 0.1% the quaternary ammonium detergent Triton® X-100. 50 mM TRIS buffer (0.5 mL, pH 7.4) would then be added to the piezoelectric sensor. While monitoring the frequency, 0.5 mL of 5-bromo-4-chloroindolyphosphate (BCIP) substrate solution (SIGMA, St. Louis, Mo., Cat. #710-3) would be added. The frequency would then be monitored. During this time a decrease in frequency in proportion to the concentration of target in the sample would be observed. The rate of change, $d\Delta f/dt$, and the overall frequency change, $\Delta f$, would be smaller than that observed for a piezoelectric sensor saturated with a biotin/alkaline phosphatase reporter conjugate. See Example 1. This would indicate that the target complex had not saturated the available surface capture reagent binding sites. A control experiment wherein the sample contained no target sequences, but in which all other steps were identical, would not exhibit a frequency change.

EXAMPLE 6

Piezoelectric detection of enzymatically polymer adsorption on the QCM

This example illustrates that urease bound to the electrodes of the QCM can induce the deposition of a pH-sensitive polymer so as to afford an easily measurable frequency change.

Anti-human IgG was adsorbed onto the gold electrodes of the QCM by immersion of the QCM in a 200 µg/mL solution of anti-human IgG for 4 hours. After this treatment a crystal was placed in the QCM cell and 0.5 mL of an aqueous solution containing 0.1% of a terpolymer comprising equimolar amounts of acrylic acid, methyl methacrylate and dimethylaminoethylmethacrylate acidified to pH=4.0. At this pH, the polymer is water soluble due to protonation of the dimethylaminoethylmethacrylate functionality. Then urea was added to a final concentration of 10 mg/mL. The addition of urea caused an increase in pH at the QCM surface that resulted in protonation of the polymer and its deposition on the QCM surface. This afforded a decrease in frequency, so that after 1 hour $\Delta f=225$ Hz.

EXAMPLE 7

Detection of a DNA target strand

This example illustrates that single stranded DNA in a sample could be detected by prior hybridization of the target analyte with a bifunctional binder conjugate comprising biotin linked to a complementary oligonucleotide and an enzyme reporter conjugate comprising a urease enzyme reporter linked to a complementary oligonucleotide. The resulting target complex would then be captured via the biotin function by an avidin film immobilized on the piezoelectric oscillator and the piezoelectric oscillator then immersed in a aqueous solution containing 0.1% amphoteric 1:1:1 terpolymer comprising acrylic acid, methyl methacrylate and dimethylaminoethyl methacrylate acidified to pH=4.0. At this pH the polymer is water soluble due to protonation of the dimethylaminoethyl methacrylate functionality. Addition of urea would result in an increase in the pH at the surface of the piezoelectric sensor, which would render the polymer isoelectric via deprotonation of the dimethylaminoethyl methacrylate functionality. The isoelectric polymer is insoluble and would adsorb onto the electrode surface of the piezoelectric sensor, thereby resulting in a measurable frequency change.

Prior to testing a hybridization buffer was prepared by mixing 6.0 mL of 20X SSC buffer (pH, 7.0), with 0.2 mL the quaternary ammonium detergent Triton® X-100 detergent (SIGMA, St. Louis, Mo.), 2.0 mL deionized formamide, 0.025 mL 1N hydrochloric acid in 12.8 mL of purified water. This would be stored at −20° C. Just before use, the hybridization buffer would be thawed and used to prepare a hybridization test milieu containing 0.5 mL of the hybridization buffer, 0.010 mL of an aqueous solution containing alkaline phosphatase free bovine serum albumin (50 mg/mL), 0.02 mL of a solution (ca. 11 ng/mL) containing a bifunctional binder reagent ($10^{11}$–$10^{12}$ copies) comprising biotin covalently linked to a synthetic oligonucleotide with a sequence complementary to a separate and distinct region of the target analyte, and 0.010 mL of an aqueous solution (ca. 1 ng/mL) of an enzyme reporter conjugate ($10^{11}$–$10^{12}$ copies) prepared with a synthetic oligonucleotide sequence complementary to a second region of the target analyte.

The synthetic oligonucleotides contained in the bifunctional binder conjugate and the enzyme reporter conjugate each possess between 18 and 200 nucleotides. The regions in the target analyte complementary to the respective sequences in the bifunctional binder conjugate and the enzyme reporter conjugate preferably are separated by greater than five nucleotides. Insertion of the binder arms into the polynucleotide capture ligands may be accomplished with techniques incorporated by reference above in the specification sections entitled "Preparation of Nucleic Acids" and "Linking Enzymes and Binders to Capture Ligands."

Concentrations of the enzyme reporter conjugate and the bifunctional binder conjugate are dependent upon the expected concentration of the target analyte to be detected. The enzyme reporter conjugate should be used in concentrations 5 to 10 fold times less than the concentration of the bifunctional binder conjugate. Furthermore, the number of available surface capture reagent binding sites on the piezoelectric oscillator should exceed the number of bifunctional binder conjugates by 10 to 1000 fold.

A sample (0.010 mL) containing a single stranded target analyte would be first denatured by mixing with 0.03 mL of purified water and then heating the solution in boiling water for 10 min. The stock target solution would be then quickly chilled in an ice bath for at least 2 min and then centrifuged at 3000 g for 3 min. Dilution of the stock target solution could be performed to prepare test samples containing lower concentrations of the target.

For testing, 20 μl portions of the denatured target samples would then be added to 0.5 mL of the above hybridization test milieu. The reaction mixture would then be then incubated at 37° C. for 20 min. Following the hybridization step, the reaction mixture would then be brought to room temperature (ca. 25° C.) and transferred to the piezoelectric sensor to capture the target complex. After equilibrating for 15 min, the test fluid would be removed, the quartz crystal washed three times with SSC wash buffer solution containing 15 mM sodium citrate, 150 mM sodium chloride, and 0.1% the quaternary ammonium detergent Triton® X-100. 50 mM TRIS buffer (0.5 mL, pH 7.4) was then added to the quartz sensor reaction well. The assay system would then be immersed in 0.5 mL of 0.1% amphoteric 1:1:1 terpolymer comprising acrylic acid, methyl methacrylate and dimethylaminoethylmethacrylate acidified to pH=4.0. At this pH, the polymer is water soluble due to protonation of the dimethylaminoethylmethacrylate functionality. Urea would then be added to a concentration of 1 mg/mL. This would result in an increase in the pH at the surface of the piezoelectric sensor due to the enzymatic formation of ammonia, rendering the polymer isoelectric via deprotonation of the dimethylaminoethylmethacrylate functionality. The isoelectric polymer is insoluble and would adsorb onto the electrode surface of the piezoelectric sensor, resulting in a measurable frequency change. The rate of change, $d\Delta f/dt$, and the overall frequency change, $\Delta f$, would be larger than those in which the sample contains no target analyte sequences and in which no frequency change is observed.

EXAMPLE 8

Detection of human IgG

This example illustrates that biological target in a sample would be detected by prior complexation with a bifunctional binder-antibody conjugate and an enzyme-antibody conjugate, followed by immobilization of the immunocomplex onto avidin films that are immobilized on the metal electrode of a piezoelectric oscillator. Subsequent treatment with a substrate that is enzymatically converted into a product that accumulates on the surface of the oscillator would result in a measurable frequency change. In this particular example, the immunoglobulin human IgG would be complexed with a biotinylated anti-human IgG and an alkaline phosphatase/anti-IgG conjugate. The immunocomplex would be bound via the biotin functionality to an avidin film immobilized onto a gold electrode of the piezoelectric oscillator. The resulting film is then exposed to BCIP and the change in frequency measured.

For detection, after capture of the immunocomplex by the piezoelectric sensor the sensor would be immersed in TRIS buffer containing BCIP. The alkaline phosphatase of the enzyme reported conjugate, which would be bound to the oscillator surface by virtue of binding of the target complex to the oscillator, would catalyze the conversion of BCIP to its insoluble dimer, whose deposition would result in a frequency change. Samples containing no human IgG, but in which all other steps were identical, would exhibit no frequency change since in this case alkaline phosphatase would not be bound to the piezoelectric sensor.

It will be apparent that the instant specification and examples are set forth by way of illustration and not limitation, and that various modifications and changes may be made without departing from the spirit and scope of the present invention.

What is claimed is:

1. A method for detecting a target nucleic acid analyte by means of a piezoelectric sensor, wherein said target nucleic acid analyte is a DNA or RNA molecule, comprising:

(a) coating a surface capture reagent consisting of streptavidin or avidin on the surface of a piezoelectric oscillator, wherein said streptavidin or avidin is directly adsorbed bonded to said oscillator surface by direct adsorption without the aid of an adhesion promoter and wherein said surface comprises a metallic gold film, to form a piezoelectric sensor;

(b) contacting a liquid sample suspected of containing said target nucleic acid analyte with an enzyme reporter conjugate and a bifunctional binder conjugate to form a target complex, said complex comprising (i) the enzyme reporter conjugate further consisting of an enzyme and a polynucleotide recognition sequence which is selected to complex with a sequence within the target nucleic acid analyte, (ii) the suspected target nucleic acid analyte, and the bifunctional binder conjugate;

(c) capturing the target complex with the surface capture reagent coated on the piezoelectric oscillator to form an assay system;

(d) separating uncaptured target complex, enzyme reporter conjugate, and bifunctional binder conjugate from the assay system;

(e) measuring the resonant frequency of the piezoelectric sensor;

(f) contacting the assay system with a signal generating substrate specific for the enzyme of the target complex to the assay system;

(g) allowing the accumulation on the surface of the piezoelectric oscillator of a signal generating product resulting from the conversion of the signal generating substrate by the enzyme; and (h) monitoring the resonant frequency of the piezoelectric oscillator caused by the accumulation of the signal generating product onto the piezoelectric sensor.

2. The method of claim 1 wherein the enzyme is selected from the group consisting of alkaline phosphatase, B-galactosidase, horseradish peroxidase, urease and glucose oxidase.

3. The method of claim 1 wherein the bifunctional binder conjugate comprises a substance which binds specifically to the surface capture reagent and a second capture ligand consisting of a polynucleotide recognition sequence that will complex with the target nucleic acid analyte.

4. The method of claim 3 wherein the substance which binds specifically with the surface capture reagent is selected from the group consisting of biotin, iminobiotin and derivatives of biotin and iminobiotin.

5. The method of claim 1 wherein the signal generating substrate is soluble and specific for the enzyme of the enzyme reporter conjugate.

6. The method of claim 5 wherein the signal generating substrate is selected from the group consisting of insoluble dyes, peroxidase enzymes, and peroxidases.

7. The method of claim 5 wherein the signal generating substrate is selected from the group consisting of S-bromo-4-chloro-3-indolylphosphate (BCIP), benezidene dyes, carbazole dyes, and napthol dyes, and phenazine methosulfate nitrobluetetrazolium.

8. The method of claim 1 wherein step (f) further comprises adding a pH sensitive polymer to the solution, said pH sensitive polymer accumulating on the piezoelectric sensor upon the conversion by the enzyme of the signal generating substrate.

9. The method of claim 1 wherein (b) and (c) may occur sequentially or simultaneously.

* * * * *